United States Patent [19]

Palazzolo

[11] Patent Number: 5,607,628
[45] Date of Patent: Mar. 4, 1997

[54] PROCESS FOR THE DUPLICATION OR CONSTRUCTION OF A COPY OF A DENTURE

[75] Inventor: Santo Palazzolo, 52 Via Alcide De Gasperi, I-95197 Catania, Italy

[73] Assignees: Santo Palazzolo; Gregorio Palazzolo, both of Catania, Italy

[21] Appl. No.: 149,937

[22] Filed: Nov. 10, 1993

[30] Foreign Application Priority Data

Dec. 10, 1992 [IT] Italy .................................. RM92A0876

[51] Int. Cl.⁶ .................................................. A61C 13/10
[52] U.S. Cl. ............................ 264/18; 264/157; 264/220; 264/222
[58] Field of Search ................................. 264/18, 17, 157, 264/220, 222

[56] References Cited

U.S. PATENT DOCUMENTS 3,217,067  11/1965  Tencate ..................................... 264/18
4,521,193  6/1985  Cialone ..................................... 264/18

Primary Examiner—Christopher A. Fiorilla
Attorney, Agent, or Firm—Wenderoth, Lind & Ponack

[57] ABSTRACT

A copy of a complete or partial denture is obtained by forming an impression of the denture in a flask with distinct impressions made in plaster for a gum base and in silicone resin for a dental arch. The duplicate of the denture is formed by formation of the teeth and of the gum base using respective polymerizable materials in the same flask.

11 Claims, 2 Drawing Sheets

PROCESS FOR THE DUPLICATION OR CONSTRUCTION OF A COPY OF A DENTURE

BACKGROUND OF THE INVENTION

1. Field of the Invention

The present invention relates to a process for the duplication, or construction of a copy, of a partial or total mobile denture supplied by the person requesting the copy.

2. Description of the Prior Art

Those wearing mobile dentures, either partial or total, require at least one other identical denture for use in case of loss, breakage or repair of the original one.

According to the present state of the art, construction of a copy of an original denture requires a preparation time almost equivalent to that for preparation of the original. The wearer has to hand over his denture to the laboratory for a considerable amount of time, ranging from one to a number of days, so that impressions can be prepared, artificial teeth chosen to be inserted in the denture, and so on, as is well known to those skilled in this field. During the whole of this period the wearer is left without a denture, resulting in serious discomfort.

At present, the second denture is manufactured using the same techniques used to construct the original, so that sittings are necessary in order to adjust the copy until the wearer is happy with it.

All this involves a waste of time, discomfort for the wearer and a cost for the new copy which is approximately the same as that of the original. In fact, according to traditional state of the art methods, the teeth are purchased ready-made and are adjusted and altered a number of times until they are as "close" as possible to those on the original denture.

SUMMARY OF THE INVENTION

The object of the present invention is to obtain a copy or duplicate of the original denture, in which fixing of resin teeth to a denture support structure in "pink resin" takes place by chemical fusion between the two resins, with formation in loco of single teeth identical to those on the denture. In this way the result obtained is novel, not only because the process for its realization is novel, but also because it is different from a denture obtained using the prior art, in which pre-existing teeth of the standard type normally available ready-finished and polished on the market are fixed into the gum cast in pink resin, without any chemical bonding between the pink resin and the tooth.

It therefore results that the copy of the denture prosthesis produced using the process according to the present invention, as well as being produced in an extremely short time, has technical characteristics which cannot be reproduced without using the new process.

In fact, as mentioned above, a further and extremely important advantage of the present invention is that the wearer of the denture, when handing the latter over to the dental laboratory, only remains without his denture for ten or twenty minutes, after which the denture is returned. Furthermore, the copy of the denture can be reproduced in an average time of about 100 minutes, guaranteeing a perfect copy of the original which usually requires no further adjustment.

An object of the present invention is therefore a process for duplication or production of a copy of an original denture formed of a gum portion and a tooth portion, including it comprises the following operations:

embedding the gum portion in a dental molding material to form a mold for the gum portion containing an impression thereof;

embedding the tooth portion in a first polymerizable resin material in a releasable contiguous relationship with the mold for the gum portion;

polymerizing said first resin material to form a mold for the tooth portion containing an impression thereof;

separating the mold for the tooth portion and the mold for the gum portion and removing the original denture therefrom;

filling the mold for the tooth portion with a second polymerizable resin material suitable for construction of artificial teeth and polymerizing the second resin material to obtain a duplicate dental arch of the original denture;

separating and cleaning each single tooth of the duplicate dental arch;

placing the single teeth in their respective positions in the mold for the tooth portion, to reform the dental arch;

filling the remaining space in the mold for the tooth portion with a third polymerizable resin suitable to form the gum base of a denture;

filling the mold for the gum portion with the third polymerizable resin suitable to form the gum base of a denture; and placing the mold for the tooth portion and the mold for the gum portion in contiguous matching relationship and polymerizing the third polymerizable resin to obtain a duplicate of the original denture.

BRIEF DESCRIPTION OF THE DRAWINGS

The invention will be more clearly described with reference to the enclosed drawings, in which.

DESCRIPTION OF THE PREFERRED EMBODIMENTS

A detailed description of the various stages of the process will now be given.

As stated above, it should be noted that, as the process only requires the presence of an original denture and a series of operations for obtaining impressions and for molding, most of the operations making up the process can be conceived to be carried out automatically using suitably controlled apparatus.

The invention will now be described with reference to apparatus presently used and found in a dental studio, but, as will be noted, at least a part of the operations can be performed automatically.

It must also be noted that the materials indicated for use in forming the duplicate denture are materials presently on sale and known to specialists in this field, but that other materials with equivalent functions can be devised and used without departing from the scope of the present invention.

In substance, the following detailed description of the process refers to its performance in a present-day dental studio, but the invention is clearly susceptible to other embodiments on an industrial level and using different materials.

Figure 1:
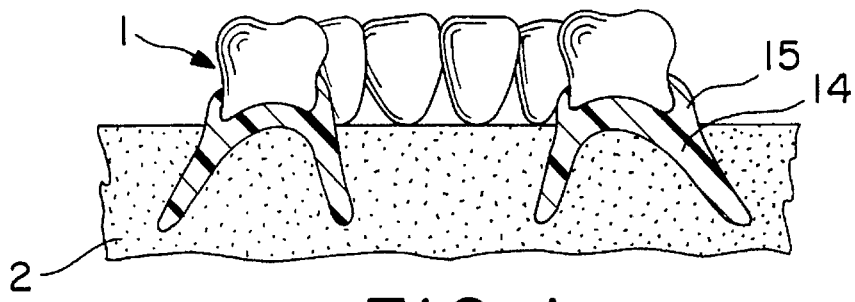
FIG. 1 is a cross-sectional view of an original denture with a gum base incorporated into a plaster base.
Figure 2:
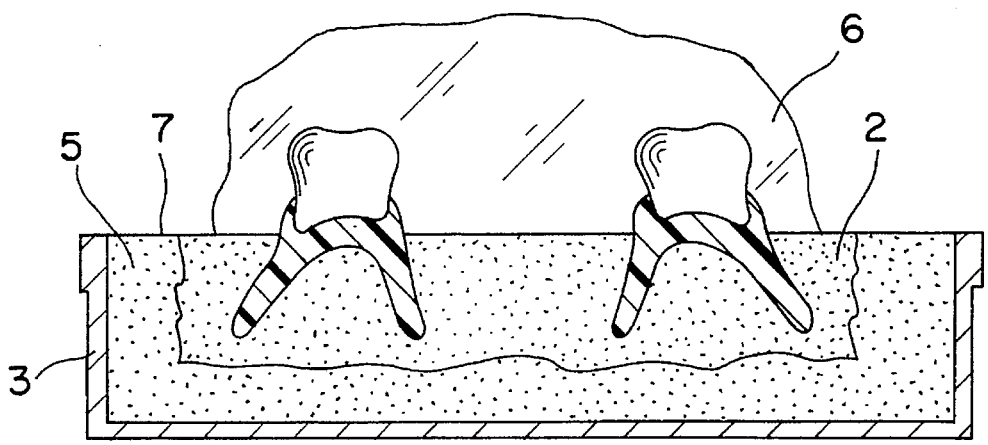
FIG. 2 is a similar view showing the plaster base fixed in the flask and the dental arch incorporated in a mold of silicon plastic.

With reference to FIG. 1, an original denture is handed over by the wearer and is indicated at 1.

The denture is made of a gum portion 14 and a tooth portion 15. The term tooth portion is intended to mean the portion beginning on an imaginary plane crossing the denture at the height at which the teeth emerge from the gum base. Consequently the tooth portion also comprises those parts of the gum base made of "pink" resin located between the teeth.

On the gum base of the denture an insulating microfilm of a releasing agent is applied. The gum portion 14 is embedded in a dental molding material to form a mold 2. As a dental molding material hard plaster is preferably used around the gum portion, up to the lower level of the teeth. Hard plaster is a material well known to dentists and is used to form impressions.

Before the plaster has completely hardened the mold 2 for the gum portion is finished, removing the excess plaster so as to free the denture from anything that may imprison it, and to ensure that it can be removed from the mold 2 without any problems.

The mold is then placed in an apparatus for forming the denture impression. In the following description and in the claims such apparatus will be represented by a flask, which comprises an upper portion 4 and a lower portion 3. The mold 2 is fixed into the lower portion 3 of the flask by pouring in liquid white scagliola plaster of a medium hardness, indicated at 5 in the drawings. Up to this point the process does not differ from the normal techniques used to fix a denture in a flask to obtain an impression.

At this point, and this, on the contrary, is a new operation with respect to the prior art, a mixture of a first polymerizable resin material is prepared, which, before it catalyzes and hardens, is applied over the tooth portion 15 of the denture, embedding it completely to form a mold 6 for the tooth portion containing the impression of the dental arch.

A polymerizable material suitable for this operation is a special dental laboratory silicon resin. As a representative, the product Silimask can be used, manufactured by SPP. This product is preferred because of its transparency to light for the photo-polymerization formation of the dental arch which will be described hereinafter.

In this manner the gum portion will be incorporated in the plaster mold 2, while the tooth portion will be incorporated in the mold 6.

The pieces containing the impressions are treated according to the process of the present invention in the following manner.

Figure 3:
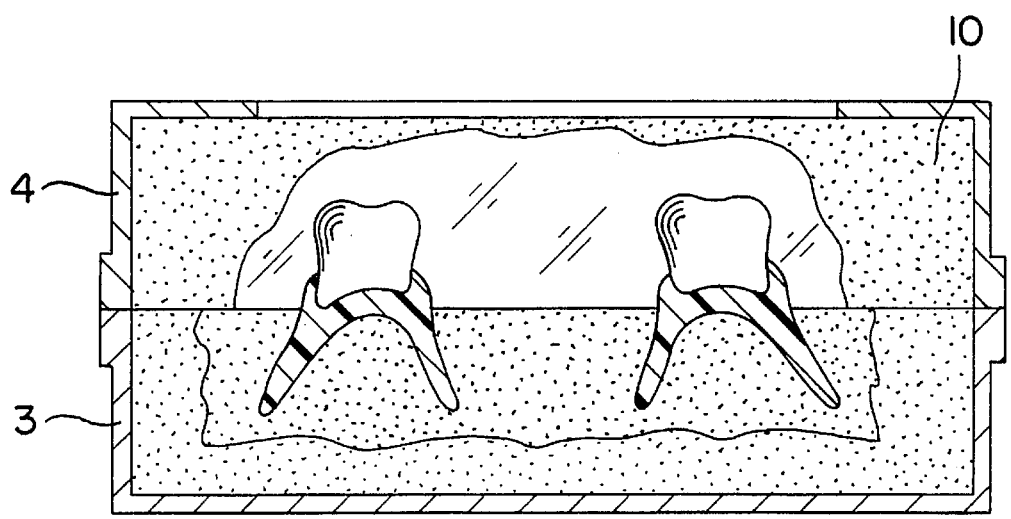
FIG. 3 is a similar view showing an operation for obtaining impressions of the dental arch and the gum base.
Figure 4:
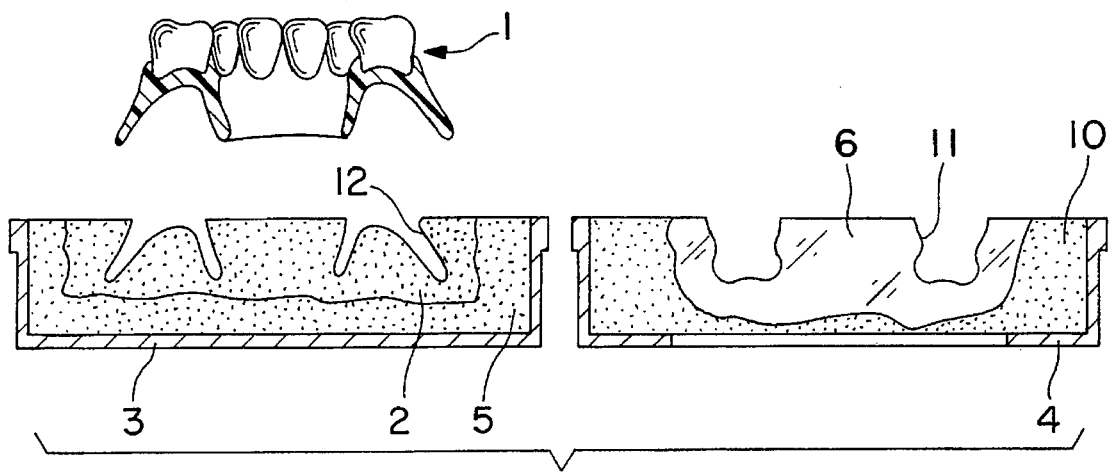
FIG. 4 shows impressions thereby obtained, with the original denture being shown removed.

An insulating film 7 of releasing agent is applied to the plaster surfaces, the upper portion 4 of the flask is closed onto the lower portion 3, and the upper portion is filled with medium hard plaster, indicated with 10. Before such plaster hardens, the flask is placed in a dental type press, to press out any excess plaster, obtaining perfect adhesion between the original denture and the mold materials (FIG. 3). After the plaster has completely hardened, on average 15 to 20 minutes, the flask is opened (FIG. 4) and the original denture 1 is extracted and returned to the client. The impression 12 of the gum base and the impression 11 of the dental arch, respectively, are thus left in the two portions 3, 4 of flask.

The central mold 6 of silicone material containing the impression 11 of the teeth is extracted and the impression 11 is filled using a second polymerizable resin for formation of teeth of the type normally used for manufacture of false teeth, such resin being made up of liquids and powders to be mixed together and well known in the field of dentistry. The resin can be a heat or photopolymerizable composition.

A preferred photopolymerizable composition is Licuplast, a known polymethylmethacrylate composition which polymerizes in 20 minutes at a 350 to 500 um light wavelength.

Figure 5:
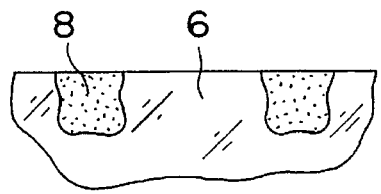
FIGS. 5 and 6 show formation of a dental arch.

The resin loaded into the impression of mold 6 is indicated at 8 in FIG. 5. Creation of the duplicate set of teeth is thus commenced, the resulting teeth being perfectly identical to the original ones.

The central mold 6 filled as indicated above is placed in a polymerizing apparatus. A type of apparatus commercially available for heat polymerization is IVOMAT manufactured by Ivoclar.

Using this apparatus, polymerization takes place in a time of 5 to 6 minutes, at a temperature of 105° to 110° C. and with a pressure of 6 atmospheres.

A photopolymerizing apparatus which can be used in this step is that commercially known as TRIAD 2000.

Figure 6:
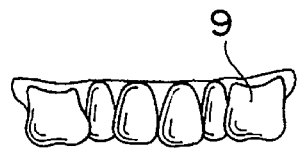
Figure 7:
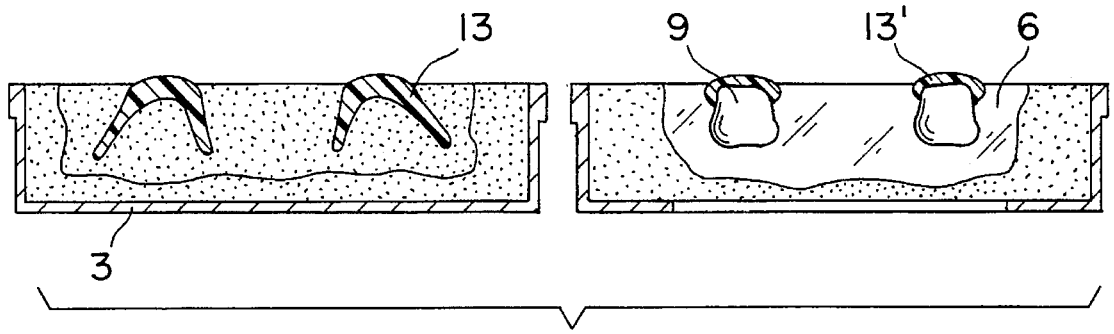
FIG. 7 shows the operation of forming the gum base for a duplicate denture.
Figure 8:
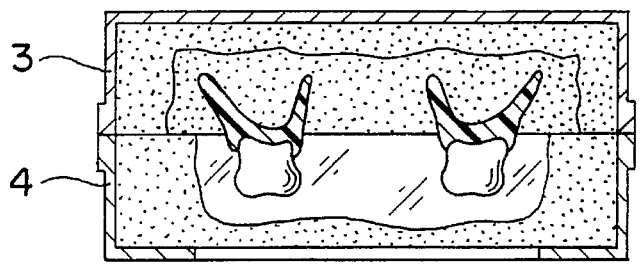
FIG. 8 shows final formation of the duplicate denture.

After polymerization, the mold 6 is extracted and the dental arch thus obtained, indicated at 9 in FIG. 6, is extracted. The central mold 6 is replaced in the upper portion 4 of the flask, FIG. 4 and FIG. 7.

The following operation is that of separating the teeth in the dental arch 9 thus obtained, cutting them out one by one using an extremely thin metal cutting wheel and cleaning them of any excess material not forming part of the teeth themselves.

The teeth 9 thus obtained are re-positioned in order in their impression 11 in the central mold 6 (FIG. 7) to restore the dental arch for the duplicate denture.

It should be noted at this point that the artificial teeth thus formed lack the heel normally found in teeth commercially available for dentures. This makes the duplicate denture manufactured according to the invention different from a copy of a denture produced according to the prior art.

At this point, after having arranged an insulating film of releasing agent on the plaster surfaces in the two portions of the flask, the hollow impressions 11 and 12 in the two portions of flask are filled up with a third polymerizable resin 13, 13', respectively, to form the gum base and to fill up the areas left free of the teeth in the impression 11 in the central mold 6. This resin, which is of the type suited for formation of the gum base, is well known in the dental field and is made up of powders and liquids to be mixed together for polymerization, an example of which is represented by the resin Meliodent, a polymethylmethacrylate resin manufactured by the company Bayer.

On completion of this operation, known as "wedging" in the field of dentistry, the flask is closed and locked in the hydraulic press mentioned above, to press out any excess resin. The flask is then fixed tightly into a special clamp and set to boil in a flask polymerizer for approximately 35 minutes. An example of a flask polymerizer is type P90 manufactured by Fratelli Manfredi.

Once the boiling operation has been completed, the flask is extracted, allowed to cool and then opened, extracting the contents. The product thus obtained is an exact duplicate of the original denture, which need only be cleaned of any excess material and polished using a traditional system.

As the adherence of the false teeth to the gum base takes place by chemical adhesion between resins, the duplicate denture obtained is without the fixing heel found in commercially available false teeth, and furthermore it shows greater resistance to separation than dentures produced using false teeth.

In the embodiment described above, the time required to form the whole duplicate denture is around 100 minutes.

EXAMPLE OF PREPARATION AND STATIC STRENGTH TEST

Following the procedure described hereinbefore a duplicate denture is prepared using a Silimask polymerizable composition for the mold to form the imprint of the dental arch and a photopolymerizable Licuplast composition for forming the duplicate dental arch.

An original prosthesis and the duplicate thereof produced according to the process of the invention were made to undergo a static strength test to verify the quality of the duplicate obtained.

The test consisted of applying a static load to a tooth in a direction inclined to the axis of the tooth, the load being increased until breaking of the tooth occurred.

During the test the prosthesis was held fixed by a clamping device.

The load was applied by an indented rod connected to a hydraulic loading apparatus.

The load applied was displayed on a loading cell,

The data were recorded on a data recording apparatus UPM60 of HBM.

The test results are listed in the following table.

TABLE 1

| Tooth No. | Denture | Load Kg. | Specification |
|---|---|---|---|
| 1 | Original | 18.3 | Tooth removed |
|   | Duplicate | 16.4 | Tooth broken |
| 2 | Original | 17.7 | Tooth removed |
|   | Duplicate | 18.6 | Tooth broken |
| 3 | Original | 26.7 | Tooth removed |
|   | Duplicate | 31.4 | Tooth removed |
| 4 | Original | 32.7 | Tooth removed |
|   | Duplicate | 35.7 | Tooth removed |

The test results showed that the duplicate denture has strength characteristics superior to the original denture (teeth 3 and 4) or comparable thereto (teeth 1 and 2). In the latter case the duplicate denture showed a different behaviour during the strength test, the teeth tending to break rather than to be removed. This is caused by the different structure of the duplicate denture with respect to the original one, due to the lack of a heel in the duplicate. The test showed that the strength of the gum-tooth connection in the duplicate is no lower than, and can be higher than in the original denture, in spite of this difference in structure.

Although the invention has been described in considerable detail, experts in the field will realize that the process can make use of equivalent techniques known to specialists in this field and to equivalent materials, without departing from the scope of the present invention.

I claim:

1. A process for duplication or production of a copy of an original denture formed of a gum portion and a tooth portion, said process comprising:

embedding said gum portion in a dental molding material to form a mold for said gum portion containing an impression thereof;

embedding said tooth portion in a first polymerizable resin material in a releasable contiguous relationship with said mold for said gum portion;

polymerizing said first resin material to form a mold for said tooth portion containing an impression thereof;

separating said mold for said tooth portion and said mold for said gum portion and removing said original denture therefrom;

filling said mold for said tooth portion with a second polymerizable resin material suitable for construction of artificial teeth and polymerizing said second resin material to obtain a duplicate dental arch of said original denture, said duplicate dental arch including plural teeth;

separating and cleaning each said tooth of said duplicate dental arch;

placing the thus separated and cleaned teeth in their respective positions in said mold for said tooth portion, to thereby reform said duplicate dental arch;

filling a remaining space in said mold for said tooth portion with a third polymerizable resin suitable to form a gum base of a denture;

filling said mold for said gum portion with said third polymerizable resin suitable to form said gum base of a denture; and placing said mold for said tooth portion and said mold for said gum portion in contiguous matching relationship and polymerizing said third polymerizable resin to obtain a duplicate of said original denture.

2. A process according to claim 1, wherein said first polymerizable resin material is a silicon-based polymerizable mixture.

3. A process according to claim 1, wherein said mold for said tooth portion is polymerized in a polymerizing machine.

4. A process according to claim 1, wherein polymerization of said third resin to form the gum base is performed in a boiler.

5. A process according to claim 1, comprising:

forming said mold for said gum portion using molding plaster around said gum portion of said original denture to obtain an impression of a gum base up to a level of a dental arch thereof, thus forming a plaster mold, and placing said plaster mold containing said original denture in a lower part of a flask and fixing said plaster mold therein by means of liquid plaster poured therein without exceeding a level of said plaster mold;

said embedding said tooth portion comprising embedding a portion of said original denture emerging from said plaster mold in said first polymerizable resin material that is suitable to form said mold for said tooth portion having an impression of said dental arch above said level of said plaster mold;

insulating a plaster surface of said lower part of said flask using a film of releasing agent;

closing a top part of said flask, pouring liquid plaster therein, pressing said lower and top parts of said flask to expel any excess plaster therefrom and setting said plaster to harden in said flask to fix said mold for said tooth portion in said top part of said flask;

opening said lower and top parts of said flask, extracting said original denture, thus leaving said impression of said gum portion in said lower part and said impression of said tooth portion in said top part of said flask;

pouring said second resin into said impression of said dental arch;

extracting said duplicate dental arch thus formed;

said separating comprising cutting;

said placing comprising arranging said teeth in said respective impressions in said mold for said tooth portion positioned in said top part of said flask and fixing said teeth in position therein by using a first part of said third resin;

said filling said mold for said gum portion comprising pouring a second part of said third resin into said plaster mold;

insulating plaster surfaces of said lower and top parts of said flask by means of a film of releasing agent;

closing and pressing together said lower and top parts of said closing flask to expel therefrom any excess said third resin; and polymerizing said third resin and thus joining said first and second parts thereof by chemical adhesion.

6. A process according to claim 5, wherein said first polymerizable resin material is a silicon-based polymerizable mixture.

7. A process according to claim 5, wherein said molding plaster is hard plaster.

8. A process according to claim 5, wherein said liquid plaster for fixing said mold for said gum portion is white scagliola plaster.

9. A process according to claim 5, wherein said liquid plaster for fixing said upper part of said flask is white scagliola plaster.

10. A process according to claim 5, wherein said mold for said tooth portion is polymerized in a polymerizing machine.

11. A process according to claim 5, wherein polymerization of said third resin to form the gum base is performed in a boiler.

\* \* \* \* \*